United States Patent [19]

Iwakura et al.

[11] Patent Number: 5,872,075
[45] Date of Patent: Feb. 16, 1999

[54] CATALYST FOR OXIDATION OF HYDROGEN, METHOD FOR SELECTIVE OXIDATION OF HYDROGEN, AND METHOD FOR DEHYDROGENATION OF HYDROCARBON

[75] Inventors: Tomoatsu Iwakura; Makoto Takiguchi, both of Ami, Japan

[73] Assignee: Mitsubishi Chemical Corporation, Tokyo, Japan

[21] Appl. No.: 907,928

[22] Filed: Aug. 11, 1997

[30] Foreign Application Priority Data

Aug. 19, 1996 [JP] Japan .................................. 8-217338

[51] Int. Cl.⁶ ............................. B01J 23/42; B01J 23/00; B01J 23/56
[52] U.S. Cl. ......................... 502/334; 502/325; 502/332; 502/339
[58] Field of Search .................................... 502/325, 332, 502/334, 339

[56] References Cited

U.S. PATENT DOCUMENTS

| | | |
|---|---|---|
| 4,435,607 | 3/1984 | Imai . |
| 4,565,898 | 1/1986 | O'Hara et al. . |
| 4,717,779 | 1/1988 | Bricker et al. . |

FOREIGN PATENT DOCUMENTS 0 730 906  9/1996  European Pat. Off. .

*Primary Examiner*—Elizabeth D Wood
*Attorney, Agent, or Firm*—Oblon, Spivak, McClelland, Maier & Neustadt, P.C.

[57] ABSTRACT

A catalyst for oxidation of hydrogen, which is characterized in that:

A. it is a catalyst having platinum supported on alumina;

B. said alumina has a BET specific surface area of from 0.5 to 6 $m^2/g$; and

C. said alumina has an ammonia adsorption of at most 5 $\mu mol/g$, is used at the time of producing an unsaturated hydrocarbon by dehydrogenation of a hydrocarbon, whereby hydrogen present in the gas mixture can selectively be oxidized, and thus, the yield can be improved particularly when styrene is produced by dehydrogenation of ethylbenzene.

3 Claims, No Drawings

CATALYST FOR OXIDATION OF HYDROGEN, METHOD FOR SELECTIVE OXIDATION OF HYDROGEN, AND METHOD FOR DEHYDROGENATION OF HYDROCARBON

BACKGROUND OF THE INVENTION

The present invention relates to a method for selectively oxidizing hydrogen present in a gas mixture formed by dehydrogenation of a hydrocarbon to produce an unsaturated hydrocarbon, and a catalyst useful for the method.

FIELD OF THE INVENTION

A process for producing an unsaturated hydrocarbon by dehydrogenation of a hydrocarbon, has been disclosed in many literatures and has been practically used on an industrial scale. For example, a process for preparing styrene by dehydrogenation of ethylbenzene is industrially practiced by means of an iron-type dehydrogenation catalyst. However, a dehydrogenation reaction is usually subject to a restriction of equilibrium, whereby it is difficult to attain a good yield. Further, the dehydrogenation reaction is an endothermic reaction, and if the reaction is carried out in an insulated reactor, the reaction temperature decreases as the reaction proceeds, whereby it is difficult to obtain the desired product in good yield.

To solve such problems, several methods have already been proposed. For example, UK Patent No. 1,404,641 discloses a process and a catalyst for selectively oxidizing hydrogen in a gas mixture comprising unreacted ethylbenzene, styrene and hydrogen after the dehydrogenation of ethylbenzene. This method is effective for the preparation of styrene, but A-type zeolite or alumina having platinum supported thereon is used as a catalyst for selective oxidation of hydrogen, and its performance is not necessarily satisfactory.

Also JP-B-4-33769, U.S. Pat. No. 4,565,898 and U.S. Pat. No. 4,717,779 disclose a method of using a catalyst having e.g. platinum, tin and lithium supported on alumina, as a catalyst for selective oxidation of hydrogen, in a similar process. However, the performance of this catalyst is also not fully satisfactory.

Further, JP-A-58-89945 and JP-A-6-298678 disclose a method for selectively oxidizing hydrogen in a gas mixture comprising styrene, ethylbenzene and hydrogen, formed by the dehydrogenation reaction of ethylbenzene, by means of a catalyst containing tin oxide, or tin oxide and an alkali metal. This catalyst is noteworthy as a catalyst employing no platinum, but its performance is not necessarily adequate.

As described above, conventional catalysts are not satisfactory in their performance as catalysts for selectively oxidizing hydrogen in a gas mixture comprising an unreacted hydrocarbon, an unsaturated hydrocarbon as a hydrogenated hydrocarbon and hydrogen, formed by the dehydrogenation reaction of a hydrocarbon.

SUMMARY OF THE INVENTION

Accordingly, it is an object of the present invention to provide a novel catalyst for oxidizing hydrogen present in such a gas mixture with higher selectivity.

The present inventors have conducted extensive studies to solve the above problems and as a result, have found that selective oxidation of hydrogen can be carried out highly efficiently by using a certain specific alumina as a carrier for supporting platinum. The present invention has been accomplished on the basis of this discovery.

Thus, the present invention provides:
1. A catalyst for oxidation of hydrogen, which is a catalyst for selectively oxidizing hydrogen in a gas mixture containing hydrogen and a hydrocarbon, and which is characterized in that:
   A. it is a catalyst having platinum supported on alumina;
   B. said alumina has a BET specific surface area of from 0.5 to 6 $m^2/g$; and
   C. said alumina has an ammonia adsorption of at most 5 $\mu mol/g$.
2. A method for selectively oxidizing hydrogen in a gas mixture containing hydrogen and a hydrocarbon by means of such a catalyst for oxidation.
3. A method for dehydrogenation of a hydrocarbon, which comprises selectively oxidizing hydrogen in a gas mixture which is obtained by subjecting a feed hydrocarbon to a dehydrogenation reaction and which comprises a dehydrogenated hydrocarbon, an unreacted feed hydrocarbon and hydrogen, by contacting the gas mixture with an oxygen-containing gas in the presence of an oxidation catalyst, and further subjecting the unreacted feed hydrocarbon to a dehydrogenation reaction, wherein a catalyst for oxidation as defined in above item 1, is used as the oxidation catalyst.

DETAILED DESCRIPTION OF THE INVENTION

Now, the present invention will be described in detail with reference to the preferred embodiments.

The catalyst which is used for the method of the present invention, is a catalyst for selective oxidation of hydrogen, which is characterized in that:

A. it is a catalyst having platinum supported on alumina;
B. said alumina has a BET specific surface area of from 0.5 to 6 $m^2/g$; and
C. said alumina has an ammonia adsorption of at most 5 $\mu mol/g$.

The alumina which is used as a carrier in the present invention, is required to have a BET specific surface area of from 0.5 to 6 $m^2/g$ and an ammonia adsorption of at most 5 $\mu mol/g$. As will be shown in Comparative Examples given hereinafter, if either the BET specific surface area or the ammonia adsorption is outside the above range, no adequate catalytic performance tends to be obtained.

Such alumina can be prepared, for example, by adding aqueous ammonia or an aqueous solution of a base such as an alkali metal carbonate to an aqueous solution of a water-soluble aluminum salt such as aluminum nitrate to obtain aluminum hydroxide, then washing, drying and preliminarily calcining it to obtain an alumina powder, and further molding this alumina powder into a proper shape by e.g. extrusion molding or tabletting, followed by calcination. Here, the calcination temperature and the calcination time are set under the conditions such that the BET specific surface area and the ammonia adsorption of the alumina would be in the above ranges, particularly preferably under the conditions such that the calcination factor (CF) would be within a range of from 0 to 5. Such a condition can be set by carrying experiments on a trial and error basis taking the above CF into consideration.

Otherwise, commercially available alumina may be calcined again, so that the BET specific surface area and the ammonia adsorption will satisfy the above specified values.

Here, as the calcination factor (CF) of alumina, one calculated by the following formula, is used.

$$CF = 9.0 - 0.00555 \times (TEMP - 1000) \times TIME$$

where CF is the calcination factor, TEMP is the calcination temperature (°C.), and TIME is the calcination time (hr).

The BET specific surface area of alumina is obtained by a method wherein from 0.5 to 1 g of alumina pulverized to from 8 to 16 mesh is packed in a sample cell of a U shape made of quartz and maintained in a 30% $N_2$/He gas stream at 250° C. for 15 minutes to carry out pretreatment of the sample, and the specific surface area is measured by a BET method by using liquid nitrogen gas at the liquid nitrogen temperature.

The ammonia adsorption on alumina can be measured as follows. Namely, from 100 to 500 mg of roughly pulverized alumina is put into a sample cell, and while supplying helium gas at a flow rate of 80 ml/min, the temperature is raised to 400° C. and maintained for 30 minutes, followed by evacuation under a reduced pressure of $10^{-2}$ Torr at 100° C., and then, ammonia gas is injected at the same temperature in an amount of about 10 ml, and the system is maintained for 15 minutes under a condition of about 70 Torr. Further, ammonia believed to be physically adsorbed, is evacuated under a reduced pressured of $10^{-2}$ Torr for 30 minutes at the same temperature, and then helium gas is supplied at a flow rate of 80 ml/min to return the pressure to atmospheric pressure, and the temperature is lowered to room temperature. Then, while supplying helium gas at a flow rate of 80 ml/min, and raising the temperature to 700° C. at a rate of 10° C./min, the gas passed through the alumina is continuously introduced into a quadrupole mass spectrometer, and desorbed ammonia is measured to determine the amount of ammonia adsorption.

As a method for supporting platinum on alumina, a method may, for example, be mentioned wherein alumina after calcination, is impregnated with an aqueous solution of a platinum salt, followed by drying and/or calcining at a temperature of from 50° to 1,000° C. The platinum salt to be used as the starting material, is not particularly limited, and a halide, a hydroxide, a sulfate or an organic salt of platinum may be employed.

The amount of platinum supported, is usually from 0.01 to 10 wt %, preferably from 0.05 to 5 wt %, based on the alumina. If the amount supported is too small, the catalytic activity for the oxidation reaction tends to be low. On the other hand, even if the amount supported is increased beyond the above range, no substantial further effects to the reaction will be obtained, and such will be economically disadvantageous.

The catalyst for oxidation of the present invention can be pre-treated with hydrogen, an inert gas such as nitrogen or helium or a gas mixture thereof, prior to initiation of the reaction.

The catalyst for oxidation of the present invention is useful for a reaction for selectively oxidizing hydrogen in a gas mixture containing hydrogen and a hydrocarbon by contacting the gas mixture with an oxygen-containing gas. Such a reaction is carried out preferably at a temperature of from 300° to 800° C., more preferably from 400° to 700° C. If the temperature is too high, the selectivity for oxidizing hydrogen tends to be low, and combustion of the hydrocarbon increases, such being undesirable. If the temperature is too low, the catalytic activities tend to be low, although the selectivity may not substantially be influenced.

A specific example of the gas mixture containing hydrogen and a hydrocarbon may be a gas mixture comprising an unsaturated hydrocarbon, an unreacted feed hydrocarbon and hydrogen, which is obtainable by a dehydrogenation reaction of a feed hydrocarbon with a dehydrogenation catalyst.

As the oxygen-containing gas, a gas containing from 1 to 100% of molecular oxygen, is employed. Specifically, air, an oxygen-enriched air or air diluted with an inert gas, may, for example, be preferably employed. Further, steam may be incorporated to the oxygen-containing gas.

A typical process to which the selective oxidation catalyst and the selective oxidation method of the present invention may be applied, is as follows.

In a first reaction zone, a dehydrogenation reaction of a feed hydrocarbon is carried out by a dehydrogenation catalyst, and then, a gas mixture containing a dehydrogenated hydrocarbon, an unreacted feed hydrocarbon and hydrogen, discharged from this first reaction zone, will be sent to a second reaction zone. In this second reaction zone, selective oxidation of hydrogen is carried out in the presence of the oxidation catalyst of the present invention by means of an oxygen-containing gas introduced anew, whereby the temperature once lowered by the first dehydrogenation reaction as an endothermic reaction will be raised, and the restriction by equilibrium of the dehydrogenation reaction will be eliminated or reduced by the consumption of hydrogen. Further, the gas discharged from this second reaction zone will be sent to a third dehydrogenation reaction zone which is similar to the first reaction zone, and dehydrogenation of an unreacted hydrocarbon will be carried out. As the temperature required for the reaction has already been recovered and the restriction by equilibrium has already been eliminated or reduced in the second reaction zone, a higher yield can be attained in the third dehydrogenation reaction zone.

If necessary, the reaction can be carried out by further adding a combination of the above selective oxidation reaction zone and the dehydrogenation reaction zone.

It is common to conduct a dehydrogenation reaction in the presence of steam. Also in the above reaction process, steam may be present.

As a typical specific example of the above dehydrogenation process, a dehydrogenation process of ethylbenzene may, for example, be mentioned. Namely, for example, a gas mixture of ethylbenzene and steam is sent to a first reaction zone, where an iron-type catalyst comprising iron and an alkali metal as the main active components, is present, and a dehydrogenation reaction is carried out at a temperature within a range of from 400° to 800° C., preferably from 500° to 700° C., under a pressure within a range of from 0.05 to 10 atm. Then, a gas mixture of an unreacted ethylbenzene, formed styrene, hydrogen and steam, will be sent to a second reaction zone. In the second reaction zone, selective oxidation of hydrogen is carried out at a temperature within a range of from 300° to 800° C., preferably from 400° to 700° C., under a pressure within a range of from 0.05 to 10 atom (absolute pressure of from about 5 kPa to about 1 MPa), in the presence of the oxidation catalyst of the present invention by means of an oxygen-containing gas introduced anew. Then, this reaction gas is sent to a third reaction zone, where dehydrogenation of unreacted ethylbenzene is carried out again by an iron-type dehydrogenation catalyst, to obtain styrene in good yield.

According to the present invention, it is possible to selectively oxidize, at high selectivity, hydrogen in a gas mixture containing an unreacted feed hydrocarbon, a formed unsaturated hydrocarbon and hydrogen, after the dehydrogenation reaction of a feed hydrocarbon. Accordingly, the restriction by equilibrium will be removed or reduced, and the decrease of the reaction temperature can be supplemented, whereby it is possible to carry out the dehydrogenation reaction in a yield substantially higher as compared with conventional dehydrogenation reactions.

Now, the present invention will be described in further detail with reference to Examples. However, it should be understood that the present invention is by no means restricted to such specific Examples.

EXAMPLE 1

Preparation of a Catalyst 3N aqueous ammonia was gradually added to an aqueous solution of aluminum nitrate $Al(NO_3)_3 \cdot 9H_2O$ at a temperature of not higher than 30° C. with stirring, to form a precipitate of a hydroxide. Upon completion of formation of the precipitate, addition of aqueous ammonia was stopped, and the formed precipitate of aluminum hydroxide was collected by filtration and washed with water. The obtained precipitate was put into a drier and dried overnight at 120° C. The dried precipitate was put into a muffle furnace and preliminary calcined at 700° C. for 5 hours. A small amount of water was added to this calcined product, and the mixture was wet-kneaded by a kneader and then formed into pellets having an average size of 2 mm in diameter×2 mm by an extruder. The pellets were dried in a drier at 120° C. overnight and then calcined in a muffle furnace at 1,300° C. or 1,400° C. for 3 hours.

The calcination factor at that time, and the BET specific surface area and $NH_3$ adsorption of obtained alumina, were 4.005, 3.2 m²/g and 4.5 μmol/g with the 1,300° C. calcined product, and 2.34, 1.4 m²/g and 2.8 μmol/g with the 1,400° C. calcined product.

To this alumina, an aqueous chloroplatinic acid hexahydrate solution corresponding to 0.2 wt % of platinum was uniformly added, and the mixture was dried under reduced pressure at 60° C. by a rotary evaporator. The product was dried in a drier at 120° C. overnight and calcined in a muffle furnace at 650° C. for 3 hours. In this manner, two types of 0.2 wt % $Pt/Al_2O_3$ catalysts having different carrier calcination temperatures were obtained.

Reaction 1 ml of the catalyst prepared as described above, was packed into a quartz tubular reactor having an inner diameter of 7 mm, and quartz chips having substantially the same particle size as the catalyst were packed on and under the catalyst. Then, reduction treatment was carried out at 500° C. for one hour while permitting a gas mixture of hydrogen and nitrogen to flow therethrough.

After the reduction treatment, the interior of the reactor was replaced with nitrogen gas, and the temperature of the catalyst layer was set to a desired temperature. Then, a gas mixture comprising styrene, ethylbenzene, water, hydrogen and air, was introduced into the reactor to initiate the reaction. The composition of the gas mixture was:

styrene/ethylbenzene/water/hydrogen/oxygen/nitrogen= 1/1/12/1/0.52/1.95 (molar ratio). Further, the space velocity in the reactor was:

GHSV=23900 hr⁻ (0° C., 1 atm)

LHSV=(styrene+ethylbenzene)=15 hr⁻¹.

After 0.5 hour from the initiation of the reaction, the gas at the outlet of the reactor and the liquid trapped in a liquid receptor were analyzed by gas chromatography to evaluate the catalyst. The results are shown in Tables 1 and 2.

The "SM+EB combustion rate (%)" in the Tables was calculated by the following formula.

$$SM + EB \text{ combustion rate}(\%) = \frac{\text{Reactor outlet } (CO \text{ mols} + CO_2 \text{ mols})/8}{\text{Reactor inlet } (EB \text{ mols} + SM \text{ mols})} \times 100$$

where EB and SM represent mols of ethylbenzene and styrene, respectively.

TABLE 1

0.2 wt % $Pt/Al_2O_3$ using $Al_2O_3$ calcined at 1,300° C. (CF = 4.005)

| Reaction temperature (°C.) | Hydrogen conversion (%) | Oxygen conversion (%) | SM + EB combustion rate (%) |
|---|---|---|---|
| 500 | 95.4 | 100 | 0.20 |
| 600 | 88.4 | 100 | 0.37 |

TABLE 2

0.2 wt % $Pt/Al_2O_3$ using $Al_2O_3$ calcined at 1,400° C. (CF = 2.34)

| Reaction temperature (°C.) | Hydrogen conversion (%) | Oxygen conversion (%) | SM + EB combustion rate (%) |
|---|---|---|---|
| 500 | 91.6 | 96.4 | 0.21 |
| 600 | 86.5 | 100 | 0.42 |

COMPARATIVE EXAMPLE 1

Duplicate Test of Catalyst A in Example 1 of U.S. Pat. No. 4,717,779

Preparation of a Catalyst 7.6 g of tin chloride was added and dissolved in 66.7 g of an aqueous solution containing 6.6 wt % of concentrated nitric acid, and the solution thereby obtained was added to 1,139.6 g of boehmite alumina (Kaiser). This solution was gradually mixed over a period of 15 seconds and then vigorously mixed for 5 minutes. The obtained material was extrusion-molded to obtain a product having a diameter of 3 mm. Then, this extrusion molded product-was dried in a drier of 95° C. for 2 hours. The dried extrusion molded product was calcined in a quartz tube at 350° C. for one hour in an air stream, further heated to 600° C. under an air stream and calcined for 3 hours. This calcined product was further heated in a muffle furnace to 1,230° C. over a period of 8 hours and then maintained for 3 hours, and then it was gradually cooled to room temperature over a period of 8 hours.

The calcination factor (CF) by this method and the BET specific surface area and $NH_3$ adsorption of the obtained extrusion molded product, were 5.1705, 10.8 m²/g and 3.7 μmol/g, respectively.

Then, a predetermined amount of a mixed solution prepared by adding 12.91 g of a chloroplatinic acid solution containing 2.54 wt % of platinum, 37.27 g of a lithium nitrate solution containing 0.88 wt % of lithium and a very small amount of concentrated nitric acid to 142.5 g of water, was added to a glass evaporator of a steam jacket type.

Then, 50 g of a product obtained by pulverizing the extrusion molded product calcined at 1,230° C. to from 0.85 to 1.0 mm, was added to the evaporator, and the evaporator was rotated at room temperature for 15 minutes, whereupon steam was introduced into the jacket of the evaporator. While supplying nitrogen to the mouth of the evaporator at a flow rate of 1 l/min, the evaporator was rotated for 2 hours, whereupon steam was stopped, and the impregnated product was taken out and dried in a drier at a temperature of 150° C. for 2 hours and then, calcined in a quartz tube. The obtained impregnated product was heated from room temperature to 650° C. over 2 hours in a stream of air bubbled through a water bubbler heated to a temperature of 65° C., and then calcined at 650° C. for one hour in an air stream and then cooled to room temperature to obtain a 0.2 wt % Pt-0.5 wt % Sn-0.2 wt % Li—Al$_2$O$_3$ catalyst.

Reaction

The reaction was carried out in the same manner as in Example 1. The results are shown in Table 3.

TABLE 3

A 0.2 wt % Pt-0.5 wt % Sn-0.2 wt % Li—Al$_2$O$_3$ catalyst (CF = 5.1705)

| Reaction temperature (°C.) | Hydrogen conversion (%) | Oxygen conversion (%) | SM + EB combustion rate (%) |
|---|---|---|---|
| 500 | 88.3 | 100 | 0.37 |
| 600 | 77.6 | 100 | 0.63 |

COMPARATIVE EXAMPLE 2

A catalyst for oxidation was prepared and evaluated in the same manner as in Example 1 except that the carrier alumina was changed to alumina obtained by melting at 2,150° C.

The calcination factor by this method was −10.14, and the BET specific surface area and NH$_3$ adsorption of the obtained alumina were at most 0.1 m$^2$/g and at most 1 μmol/g, respectively. The results are shown in Table 4.

TABLE 4

A 0.2 wt % Pt-Al$_2$O$_3$ catalyst using alumina obtained by melting (CF = −10.14)

| Reaction temperature (°C.) | Hydrogen conversion (%) | Oxygen conversion (%) | SM + EB combustion rate (%) |
|---|---|---|---|
| 500 | 45.1 | 46.4 | 0.08 |
| 600 | 48.9 | 54.8 | 0.19 |

COMPARATIVE EXAMPLE 3

Preparation of a Catalyst 3N aqueous ammonia was gradually added to an aqueous solution of aluminum nitrate Al(NO$_3$)$_3$.9H$_2$O at a temperature of not higher than 30° C. with stirring, to form a precipitate of a hydroxide. Upon completion of formation of the precipitate, addition of aqueous ammonia was stopped, and then the formed precipitate of aluminum hydroxide was collected by filtration and washed with water. The obtained precipitate was put into a drier and dried at 120° C. overnight. The product was put into a muffle furnace and preliminary calcined at 700° C. for 5 hours. A small amount of water was added to this calcined product, and the mixture was wet-kneaded by a kneader for 2 hours and then formed into pellets having an average size of 2 mm in diameter×2 mm by an extrusion molding machine. The pellets were dried in a drier at 120° C. over night and then calcined in a muffle furnace at 1,200° C. for 3 hours.

The calcination factor (CF) by this method was 5.67, and the BET specific surface area and NH$_3$ adsorption of the obtained alumina were 5.0 m$^2$/g and 6.7 μmol/g, respectively. To this alumina, an aqueous chloroplatinic acid hexahydrate solution corresponding to 0.2 wt % of platinum was uniformly added, followed by drying under a reduced pressure by a rotary evaporator at 60° C. Then, it was dried in a drier at 120° C. over night and then calcined in a muffle furnace at 650° C. for 3 hours to obtain a 0.2 wt % Pt/Al$_2$O$_3$ catalyst.

Reaction

Preparation of a catalyst for oxidation and evaluation were carried out in the same manner as in Example 1 except that the catalyst was changed to the one obtained as described above.

The results are shown in Table 5.

TABLE 5

A 0.2 wt % Pt/Al$_2$O$_3$ catalyst using alumina calcined at 1,200° C. (CF = 5.67)

| Reaction temperature (°C.) | Hydrogen conversion (%) | Oxygen conversion (%) | SM + EB combustion rate (%) |
|---|---|---|---|
| 500 | 90.3 | 100 | 0.33 |
| 600 | 58.0 | 100 | 1.10 |

EXAMPLE 2

Preparation of a catalyst for oxidation and evaluation were carried out in the same manner as in Example 1 except that calcination of the carrier alumina was changed to 1,200° C. for 8 hours. The results are shown in Table 6. The calcination factor by this method was 0.12, and the BET specific surface area and NH$_3$ adsorption of the obtained alumina were 4.7 mg/g and 5.0 μmol/g, respectively.

TABLE 6

A 0.2 wt % Pt/Al$_2$O$_3$ catalyst using alumina calcined at 1,200° C. (CF = 0.12)

| Reaction temperature (°C.) | Hydrogen conversion (%) | Oxygen conversion (%) | SM + EB combustion rate (%) |
|---|---|---|---|
| 500 | 92.2 | 100 | 0.28 |
| 600 | 81.0 | 100 | 0.55 |

We claim:

1. A catalyst for oxidation of hydrogen, which is a catalyst for selectively oxidizing hydrogen in a gas mixture containing hydrogen and a hydrocarbon, and which is characterized in that:

A. it is a catalyst having platinum supported on alumina;

B. said alumina has a BET specific surface area of from 0.5 to 6 m$^2$/g; and

C. said alumina has an ammonia adsorption of at most 5 μmol/g.

2. The catalyst for oxidation of hydrogen according to claim 1, wherein said alumina is alumina calcined under a condition such that a calcination factor (CF) represented by the following formula is within a range of from 0 to 5:

$$CF = 9.0 - 0.00555 \times (TEMP - 1000) \times TIME$$

where CF is the calcination factor, TEMP is the calcination temperature (°C.), and TIME is the calcination time (hr).

3. The catalyst for oxidation of hydrogen according to claim 1, wherein the amount of platinum supported is from 0.01 to 10 wt %, based on the alumina.

* * * * *